US012558114B2

(12) United States Patent
Schneider et al.

(10) Patent No.: US 12,558,114 B2
(45) Date of Patent: Feb. 24, 2026

(54) SURGICAL INSTRUMENT AND STEERING GEAR FOR SAME

(71) Applicant: KARL STORZ SE & CO. KG, Tuttlingen (DE)

(72) Inventors: Janosz Schneider, Donaueschingen (DE); Dominik Längle, Mülheim (DE); Jochen Stefan, Wald (DE); Christina Specker Heiß, Emmingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 207 days.

(21) Appl. No.: 18/291,373

(22) PCT Filed: Jul. 25, 2022

(86) PCT No.: PCT/EP2022/070789
§ 371 (c)(1),
(2) Date: Jan. 23, 2024

(87) PCT Pub. No.: WO2023/006663
PCT Pub. Date: Feb. 2, 2023

(65) Prior Publication Data
US 2025/0114113 A1     Apr. 10, 2025

(30) Foreign Application Priority Data

Jul. 28, 2021     (DE) .................... 10 2021 119 524.1

(51) Int. Cl.
A61B 17/29          (2006.01)
(52) U.S. Cl.
CPC ...... A61B 17/29 (2013.01); A61B 2017/2913 (2013.01); A61B 2017/2923 (2013.01)

(58) Field of Classification Search
CPC ............ A61B 17/29; A61B 2017/2913; A61B 2017/2923; A61B 2017/00323;
(Continued)

(56) References Cited

U.S. PATENT DOCUMENTS 5,454,827 A     10/1995  Aust et al.
7,699,855 B2     4/2010  Anderson et al.
(Continued)

FOREIGN PATENT DOCUMENTS

DE     102019121092 A1     2/2021
WO        2014004242        1/2014
(Continued)

OTHER PUBLICATIONS

International Search Report, Application No. PCT/EP2022/070789, mailed Nov. 22, 2022. ISA/European Patent Office.
(Continued)

*Primary Examiner* — Brooke Labranche
(74) *Attorney, Agent, or Firm* — Honigman LLP

(57)          ABSTRACT
A steering gear for a surgical instrument includes two motorized drives designed to spatially align a wobble plate via the adjustment angle of the two drives, which is designed to control a distal angling mechanism of the surgical instrument. A first of the two drives has a first motor, which drives a drive pinion via a driveshaft, which engages with a lateral toothing of a first toothed rack, driving a first transmission pinion of a first double gear. A second of the two drives has a second motor driving a drive pinion via a driveshaft, which engages with a lateral toothing of a second toothed rack and drives a second transmission pinion of a second double gear wheel. The wobble plate is arranged between the two bevel gear rims, which are facing one another and lie on a common axis.

15 Claims, 6 Drawing Sheets

(58) Field of Classification Search
CPC .. A61B 2017/00327; A61B 2017/2912; A61B
1/0052; A61B 1/0057; A61B 1/008; A61B
2034/301; A61B 2034/305; A61B 34/30;
A61B 34/71
See application file for complete search history.

(56) References Cited

U.S. PATENT DOCUMENTS

| | | | |
|---|---|---|---|
| 10,105,128 B2 | 10/2018 | Cooper et al. | |
| 2005/0090809 A1 | 4/2005 | Cooper et al. | |
| 2008/0221391 A1 | 9/2008 | Weitzner et al. | |
| 2021/0077213 A1* | 3/2021 | Gomez | A61B 34/35 |

FOREIGN PATENT DOCUMENTS

| | | |
|---|---|---|
| WO | 2020218920 A2 | 10/2020 |
| WO | 2021127686 A1 | 6/2021 |

OTHER PUBLICATIONS

International Preliminary Report on Patentability for PCT/EP2022/070789, issued Jan. 18, 2024.

* cited by examiner

SURGICAL INSTRUMENT AND STEERING GEAR FOR SAME

CROSS-REFERENCE TO RELATED APPLICATIONS

This application is the U.S. national stage of PCT/EP2022/070789 filed on Jul. 25, 2022, which claims priority of German Patent Application No. 10 2021 119 524.1 filed on Jul. 28, 2021, the contents of which are incorporated herein.

TECHNICAL FIELD

The disclosure relates to a surgical instrument and a steering gear for same.

BACKGROUND

The prior art has disclosed surgical instruments which can be guided by hand or by a robot and which comprise tools, the tool tip of which can be pivoted by means of a plurality of meshing pivot members. These pivot members are connected by way of a multiplicity of steering wires or steering cables in order to attain delicate tool control. A more uniform force distribution in all angling directions can be obtained by way of a plurality of thin steering wires in comparison with a few thicker steering wires.

For example, a generic surgical instrument is known from U.S. Pat. No. 5,454,827, in which the distal-side pivot members are coupled via four steering wires to a spatially adjustable wobble plate arranged on the proximal side, in such a way that a movement of the spatially adjustable wobble plate causes a corresponding relative movement of the distal-side pivot members and hence a pivoting of the tool tip, with the movement of the spatially adjustable wobble plate being implemented manually by way of a type of joystick that is directly coupled therewith.

The design of the drive for the steering wires with the spatially adjustable wobble plate, on which all four steering wires are mounted, is advantageous in that this enables a spatially compact structure and only requires the movement of one component to address all steering wires.

Disadvantages of this known structure include the use of only a small number of steering wires, specifically only four steering wires, and also the purely manual actuatability of the spatially adjustable plate serving as the drive for the steering wires, whereby a sensitive and reproducible adjustment of the distal-side pivot members is hardly possible.

U.S. Pat. No. 7,699,855 has disclosed a surgical instrument having an interface that enables the connection of the instrument to a robotic arm. In this case, all drives controlling the instrument are arranged in the robotic arm. The transfer of the rotary angles from drives to the instrument is implemented by way of coupling plates in a common separation plane.

WO 2014/004 242 likewise describes such an interface, wherein the drives are installed in the robotic arm.

The aforementioned design is linked to a complex structure and an indirect control afflicted by play. The drives are not arranged directly in the surgical instrument, resulting in a nonlinear transmission behavior during the control of the wobble plate, which can only be modeled poorly in software.

U.S. Pat. No. 10,105,128 B2 also discloses a control of such a tool tip; in that case, this is implemented by way of a mechanism comprising toothed lock washer segments and joint rods for transmitting the movement of the drives to the wobble plate.

SUMMARY

Proceeding from this prior art, it is an object of the present disclosure to provide an improved steering gear for a surgical instrument which has a drive of the spatially adjustable wobble plate with a linear transmission behavior and a space-saving structure at the same time.

This object is achieved by a steering gear having the features of claim 1.

The further object of providing a surgical instrument whose spatially adjustable wobble plate is driven by a structurally simple and space-saving steering gear is achieved by the surgical instrument having the features of independent claim 11.

Developments and preferred embodiments of the steering gear and the surgical instrument are defined in the dependent claims.

A first embodiment of the steering gear according to the disclosure for a surgical instrument comprises two motorized drives. It is designed to spatially align a wobble plate by way of the adjustment angles of the two drives, the wobble plate being designed to control a distal angling mechanism of the surgical instrument.

According to the disclosure, a first of the two drives comprises a first motor which drives a drive pinion via a drive shaft, said drive pinion meshing with a lateral toothing of a first gear rack and driving a first transmission pinion of a first double gear wheel made of the transmission pinion and a bevel gear rim via an end toothing of the gear rack.

Further, a second of the two drives comprises a second motor which drives a drive pinion via a drive shaft, said drive pinion meshing with a lateral toothing of a second gear rack and driving a second transmission pinion of a second double gear wheel made of the transmission pinion and a bevel gear rim via an end toothing of the gear rack. In this case, the wobble plate is arranged between the two bevel gear rims which face one another and are located on a common axis A.

Respective orientations of the drive axes or motors can be defined in virtually any desired manner independently of one another and in relation to a plane defined by the longitudinal axis B and the common axis A, by virtue of a toothing of the drive pinion with the lateral toothing being formed in appropriately adjusted fashion depending on the orientation of the respective drive axis. Available installation space can be optimally exploited in this way. If the drive axes run perpendicular, which is to say at right angles, to the plane defined by the longitudinal axis B and the common axis A, the drive pinion may advantageously—but need not—form a spur toothing with the lateral toothing. If the orientation of the drive axes deviates from the 90° with respect to the plane defined by the longitudinal axis B and the common axis A, the meshing between the drive pinion and lateral toothing can be provided, for example, by a helical toothing with appropriate angling at the drive pinion and/or lateral toothing.

As a result of the arrangement of the motors offset by 90° from the common axis of the bevel gear rims made possible by the disclosure, horizontal installation space in relation to the alignment of the wobble plate is saved in the direction of the common axis A of the bevel gear rims.

In a preferred embodiment of the steering gear according to the disclosure, a drive axis C of the first motor may be present parallel to a drive axis C' of the second motor, with the drive axes running perpendicular, which is to say at right angles, to the common axis A. A so-called axially parallel arrangement of the motors enables a compact and hence space-saving arrangement of the components of the steering gear. Further, the parallel arrangement of the motors achieves an arrangement close to the main axis of the surgical instrument and hence improves the force transmission.

In a further embodiment of the steering gear according to the disclosure, the wobble plate may be coupled to a third gear wheel. The third gear wheel as part of the wobble plate gear meshes with the two bevel gear rims of the two double gear wheels. The axis of rotation D of the third gear wheel is at right angles to the common axis A of the driven double gear wheels. Advantageously, the three meshing gear wheels transmit any movement of the two driven gear wheels directly to the third gear wheel coupled to the spatially adjustable wobble plate, with the result that the adjusting movements of the drives can be transmitted thereby to the wobble plate, which can be tilted or pivoted about both the common axis A and the axis of rotation D as a result.

Additionally, in a further embodiment of the steering gear according to the disclosure, the wobble plate can be coupled to a fourth gear wheel which is coupled to the two bevel gear rims of the two double gear wheels and arranged on the side facing away from the third gear wheel. As a result, the all-round toothing chain is closed and ensures a uniformly all-round force distribution without play.

In yet a further embodiment of the steering gear according to the disclosure, the gear rack is elongate and cuboid, with narrow end faces, two short and two long, of which one long end face, the longitudinal end face, carries an end toothing. Side faces arise accordingly, the one of which carries a lateral toothing.

In each case, the lateral toothing meshes with a drive pinion, with each drive pinion being connected via a respective drive shaft to a respective one of the motors. The gear rack is a double gear rack, in which two toothing profiles face away from one another at right angles. This brings about a good and low-loss force transmission from the motor to the gear components, and hence precise controllability of the wobble plate.

In a preferred embodiment, the steering gear may comprise a bearing plate with a respective guide device for each gear rack, each gear rack being mounted in the respective guide device so as to be longitudinally mobile perpendicular to the common axis A and perpendicular to the drive axes of the motors. With the end toothing, the gear rack is arranged on the top side of the bearing plate—that is the side on which the double gear wheels with the transmission pinions are also arranged. Accordingly, the motors are arranged on an underside of the bearing plate. As a result of the bearing plate, the gear rack force transmission component has a secure mount, with the result that the force transmission can work without jamming.

In a further embodiment of the steering gear according to the disclosure, provision is made for the guide device or both of the guide devices each being provided by a guide groove located in the bearing plate and running perpendicular to the common axis A and perpendicular to the drive axes of the motors. In this case, the guide groove accommodates, like a projection, the lower portion of the narrow side of the gear rack which faces away from the end toothing. As a result, the gear rack is securely guided in its linear movement and the force transmission is low loss.

In an alternative or better in addition, a guide device can also be formed by a guide block arranged on the top side of the bearing plate. Said guide block is positioned and designed such that it has a lateral guide groove running perpendicular to the common axis A and perpendicular to the drive axes of the motors. A longitudinal rail of the gear rack present on the side face of the gear rack facing away from the lateral toothing is accommodated in said guide groove. This allows the gear rack to carry out the desired linear movement without jamming.

Yet a further embodiment of the steering gear according to the disclosure provides for the respective side faces of the gear racks with the lateral toothing to face the respective associated double gear wheel. The arrangement of the toothings on two faces (side and narrow side) of the gear rack at right angles to one another enables a space-saving force transmission of the drive force, which requires fewer components, from the motors to the gear wheels.

Alternatively, depending on the structural requirements of the surgical instrument or a connection to a robotic arm, other arrangements of the motors or components connecting the motors to the double gear wheels may be provided. Thus, the gear rack may also have an inverted embodiment, with the result that the lateral toothing is present on the side of the gear rack facing away from the double gear wheels and the guide rail is precisely present on the side facing the double gear wheels.

Further, each double gear wheel may comprise a bevel gear with the bevel gear rim which is connected to the transmission pinion with toothing all around via a gear shaft which extends along the common axis A. The combination of transmission pinion and bevel gear rim brings about a direct transmission of the movement initiated by the drive to the respective gear wheels of the wobble plate gear.

In yet a further embodiment of the steering gear according to the disclosure, the gear shaft is rotatably mounted in a bearing eye component, wherein the bearing eye component is fastened to the bearing plate and aligned in relation to the axis of rotation A of the double gear wheel mounted in the bearing eye component with the gear shaft. In conjunction with the further components of transmission pinion and bevel gear rim, this also attains a linear transmission of the movement initiated by the drive to the respective gear wheels of the wobble plate gear.

The disclosure also relates to a surgical instrument comprising a shaft, an actuation unit arranged at the proximal end of the shaft, and a tool arranged at the distal end of the shaft. The tool comprises a tool tip which can be angled by means of a distal angling mechanism. The angling mechanism can be controlled or aligned by means of a wobble plate that is spatially alignable by means of two drives, for the purposes of which the surgical instrument comprises a steering gear according to the disclosure, wherein the two drives are part of the steering gear according to the disclosure, which is designed to transfer the adjustment angles of the two drives to the spatial alignment of the wobble plate in order thus to control the angling mechanism.

As a result of the steering gear according to the disclosure, the surgical instrument can be constructed in structurally simple and space-saving fashion, with the result that a simple connection to a robotic arm can be enabled, in the case of which the movement of the drives can be transmitted linearly to the tool tip. The consequence is a precisely controllable use of the surgical instrument.

To three-dimensionally adjust the spatially adjustable wobble plate despite the coupling for conjoint rotation with the third gear wheel which meshes with the two bevel gear rims of the two double gear wheels, which is to say to be able to overlay the tilt or pivot movements with a rotation of the wobble plate about the longitudinal axis, a preferred embodiment of the surgical instrument can provide for the wobble plate, via a bearing ring, to be mounted so as to be rotatable about the longitudinal axis B of the shaft in a steering ring that is coupled for conjoint rotation with the third gear wheel. For the rotative coupling of the wobble plate with a main shaft running coaxially to a longitudinal axis B of the shaft, the wobble plate can be gimbal-coupled to the main shaft. Hence, the tool tip can be rotated about the longitudinal axis of the shaft by means of the wobble plate, in addition to the pivoting or tilting relative to the longitudinal axis of the shaft by way of the two drives and by way of the main shaft, without the steering wires becoming twisted.

To form the gimbal mount of the spatially adjustable wobble plate, an embodiment of the surgical instrument according to the disclosure may provide for the wobble plate to be pivotably mounted on a universal joint plate by way of two bearing pins arranged offset from one another by 180°, wherein the universal joint plate is pivotably mounted on the main shaft by way of two bearing pins arranged offset from one another by 180°, and wherein the bearing pins of the wobble plate and universal joint plate are arranged offset from one another by 90°. The gimbal suspension enables a movement guidance in all three spatial axes, whereby the tool tip can be controlled in targeted fashion. As an alternative to a universal joint plate with two pin pairs crossed at right angles for the gimbal mount of the wobble plate on the main shaft, an advantageous embodiment may, for gimbal mounting purposes, provide for the main shaft to comprise two guide grooves present in its outer face, said guide grooves extending diametrically and along the main shaft, wherein the wobble plate, which has an annular embodiment with an outer side and an inner side, comprises two diametrically and radially inwardly pointing pins arranged on the wobble plate. Each one of the two pins securely assembled on or in the wobble plate engages in one of the guide grooves introduced in the main shaft on both sides, with the result that a rotary angle of the shaft is transferable to the wobble plate. Advantageously, this yields a rotationally rigid connection between the main shaft and wobble plate, which allows a rotary angle transfer even in the case of a large angle offset (±40° and more) and axial offset, and which in the process has a very compact design, and is simple to produce and assemble. However, for a gimbal mount of a wobble plate on a main shaft, use could in principle also be made of a curved tooth coupling despite a relatively small angular offset, a constant velocity joint despite the complicated fabrication and complex assembly, or an integrally bonded coupling, which is frequently linked to a play-affected rotary angle transfer.

Also, a further embodiment of the surgical instrument according to the disclosure provides for the fourth gear wheel to be coupled to the wobble plate via a bearing ring with the steering ring, wherein the fourth gear wheel is freely rotatable vis-à-vis the third gear wheel. This fourth gear wheel closes the all-round toothing chain and thus ensures a uniformly all-around and play-free force distribution.

In a further embodiment of the surgical instrument according to the disclosure, an actuation element is axially displaceably mounted in the shaft and is operatively connected to the actuation unit on the proximal side. The distal angling mechanism of the tool tip which is able to be angled consists of pivot members which are arranged at the distal end of the shaft and connected to the wobble plate of the steering gear by way of steering wires running in the longitudinal direction of the shaft. The steering wires can be clamp-mounted on the wobble plate by means of a clamping connection so that, in the case of damage, the steering wires can easily be replaced. Alternatively, the steering wires may also be fastened to the wobble plate by means of welding or crimping, for example.

In a further embodiment of the surgical instrument according to the disclosure, a radial distance of the steering wires from the longitudinal axis of the shaft is greater at the wobble plate than at the proximal end of the shaft, from where the steering wires emerge. In this case, the steering wires may extend directly to the wobble plate from the proximal end of the shaft, with the steering wires running at an angle with respect to the wobble plate that deviates from 90°. Alternatively, a fan plate can be arranged on the main shaft distally in front of the wobble plate, said fan plate increasing the radial distance of the steering wires, which emerge from the proximal shaft end, from the longitudinal axis of the shaft such that the steering wires run approximately parallel to one another between the fan plate and the wobble plate and, in relation to a plate surface of the wobble plate, form an angle of approx. 90°. The variant without fan plate may be preferred on account of the smaller installation space requirements. As a result of increasing the radial distance of the steering wires from the longitudinal axis of the shaft, for example from a diameter of 4 mm to a diameter of 18 mm, it is not only the assembly and fabrication of the drive of the steering wires which is equipped with a spatially adjustable plate that is simplified, but also the adjustment angles of the spatially adjustable plate or, as a consequence of the increased lever, the forces required for angling that are reduced, which is done in order to obtain a pivot angle of the tool tip that corresponds to the extent of the diameter increase.

Cutouts for the steering wires and the actuation element may be formed in the gear rims of the third gear wheel and fourth gear wheel in order to avoid a collision of the gear wheels with the steering wires and optionally with the actuation element when the third and fourth gear wheel are pivoted relative to the longitudinal axis of the shaft.

The surgical instrument according to the disclosure is advantageous in that many thin steering wires can be used to control the pivotable tool tip and that, on account of the motorized drive for the spatially adjustable plate on which the steering wires are mounted proximally, this control is sensitive, precise and reproducible.

Further embodiments, and some of the advantages connected to these and further embodiments, are rendered clear and better understandable by the following detailed description which makes reference to the attached figures. Objects or parts thereof which are substantially the same or similar may be provided with the same reference signs. The figures are merely a schematic illustration of an embodiment of the disclosure. An exemplary embodiment of the disclosure is depicted in the drawings. The drawings, the description, and the claims contain numerous features in combination. A person skilled in the art will advantageously also consider the features on an individual basis and combine them to form further advantageous combinations.

DETAILED DESCRIPTION OF PREFERRED EMBODIMENTS

Figure 1:
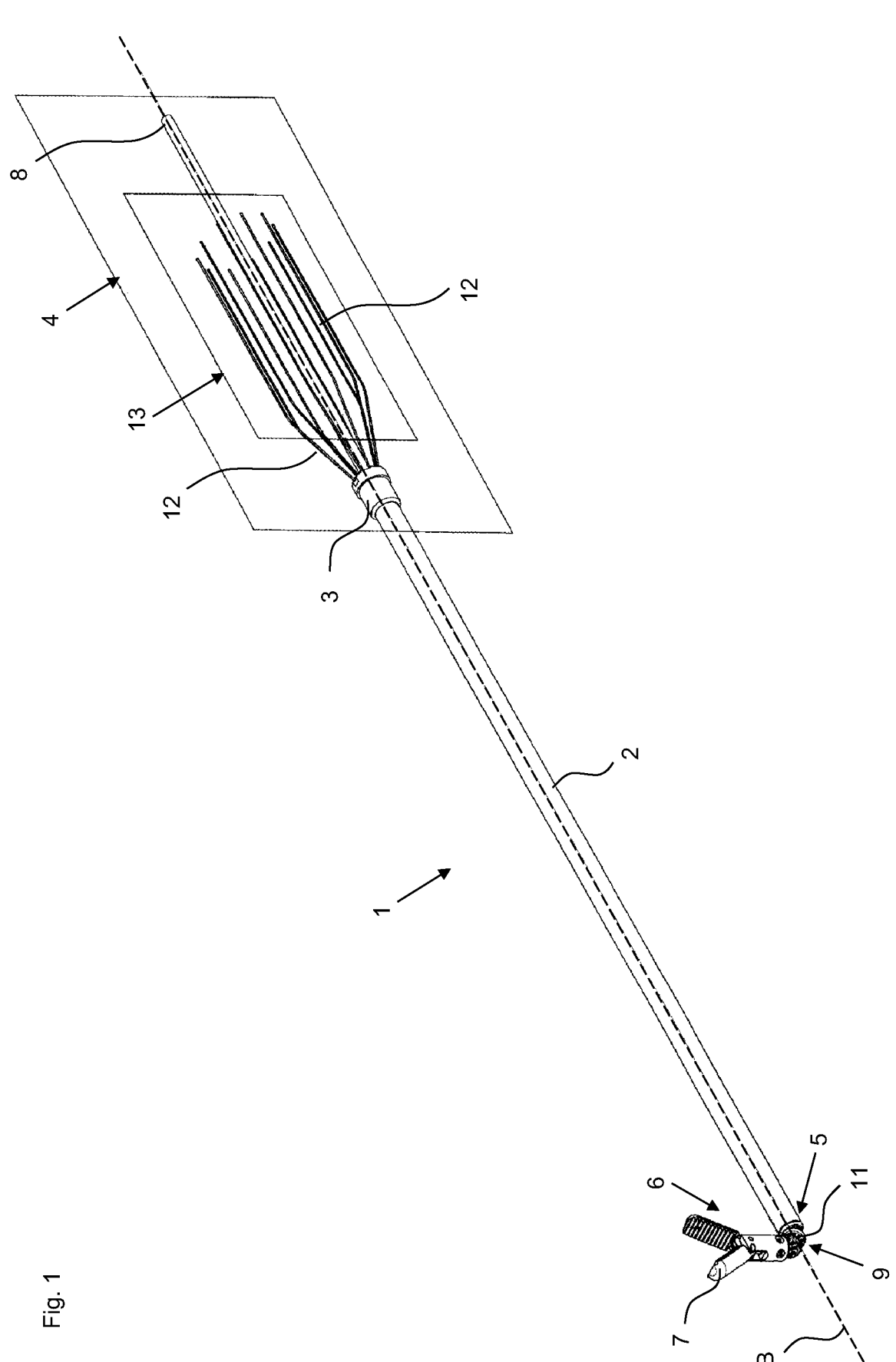
FIG. 1 shows a perspective view of the surgical instrument with a schematically depicted actuation unit.

FIG. 1 shows a surgical instrument 1 with a hollow shaft 2 which comprises a schematically depicted actuation unit 4 arranged at the proximal end 3 of the shaft 2 and a tool tip 6 arranged at the distal end 5 of the shaft 2. The tool tip 6 is connected to an instrument 7, wherein the instrument 7 is actuatable by way of an actuation element 8 which is axially displaceably mounted in the shaft 2 and, on the proximal side, operatively connected to the actuation unit 4. The actuation unit 4 can be a manually actuatable handle, or else an assembly designed for robotic use, which is to say an assembly that is actuatable without manual assistance as well.

For example, the instrument 7 of the tool tip 6 can be a tool provided with jaw parts, as depicted in FIG. 1, or else an endoscope, an applicator, or the like.

The tool tip 6 is pivotable relative to the longitudinal axis B of the shaft 2 by way of a joint mechanism 9, wherein the joint mechanism 9 consists of pivot members 11 which are arranged at the distal end of the shaft 5 and connected via steering wires 12 running in the longitudinal direction of the shaft 2 to a drive 13 arranged at the proximal end 3 of the shaft 2, in such a way that a movement of the proximal-side drive 13 causes a corresponding relative movement of the distal-side pivot members 11 and hence a pivoting of the tool tip 6.

Even though exclusive use is made of the term steering wires 12 hereinabove and below, from a functional point of view use can also be made of steering cables, which is why the used term steering wires 12 should also be read and understood synonymously as steering cables.

The axially displaceable actuation element 8, which is mounted in the shaft 2 and serves to actuate the instrument 7 for example consisting of two jaw parts, is in the form of a push/pull rod in the embodiments depicted.

In the surgical instrument 1 depicted in the drawings and described below, the drive 13 for the steering wires 12 is in the form of a motorized drive 13.

The core of the drive 13 is a spatially adjustable wobble plate 14 (FIGS. 2 and 4 to 6), on which the steering wires 12 are mounted such that a displacement of the wobble plate 14 causes a pivoting of the tool tip 6 by way of the steering wires 12 mounted on said wobble plate. The wobble plate 14 can be displaced by means of the motorized drive 13.

By using a motorized drive 13 for the wobble plate 14, it is possible to control the steering wires 12 for pivoting the distal-side pivot members 11 or tool tip 6 precisely, sensitively in very small increments, and also in reproducible fashion. Moreover, the number of steering wires 12 to be used for a motorized steering gear 13 can be chosen quite freely.

Figure 2:
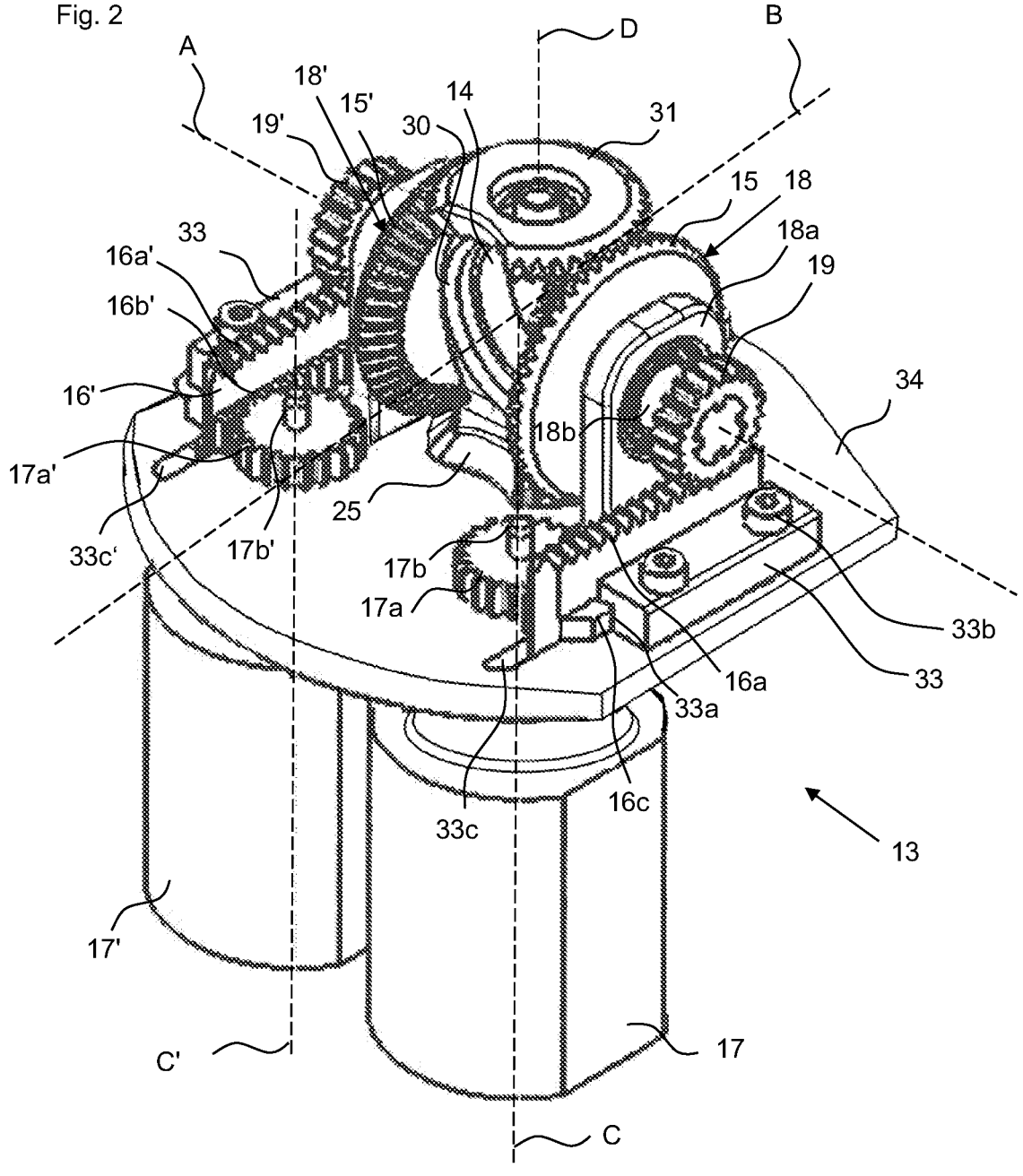
FIG. 2 shows a perspective detailed view of a first embodiment of the steering gear according to the invention.

FIG. 2 depicts the steering gear 13 in simplified fashion, wherein the steering gear 13 comprises a wobble plate 14 at the center. Four gear wheels arranged diametrically with respect to the wobble plate 14 are connected to the wobble plate 14. In FIG. 2, a third gear wheel 25 and a fourth gear wheel 31 are arranged above and below the wobble plate 14 and operatively coupled to the wobble plate 14. That is to say, a movement of one of these gear wheels 25, 31 has a direct movement of the wobble plate 14 as a consequence. Double gear wheels 18, 18' respectively arranged to a left and right side mesh with the gear wheels 25, 31. To this end, the double gear wheels 18, 18' comprise bevel gear rims 15, 15', which mesh directly in the gear rims of the third gear wheel 25 and fourth gear wheel 31. The double gear wheels 18, 18' comprise transmission pinions 19, 19' in opposite directions along their center axis A, which also forms the common axis of rotation of both double gear wheels 18, 18'. These transmission pinions 19, 19' are connected to a gear shaft 18*b* which is rotatably mounted in a bearing eye component 18*a* via a bearing ring 36 (cf. FIG. 5). The gear shaft 18*b* connects the two components of bevel gear rim 15, 15' and transmission pinion 19, 19', whereby a double gear wheel 18, 18' is formed in each case. This applies to both double gear wheels 18, 18'. The transmission pinions 19, 19' each interact with a gear rack 16, 16', with the transmission pinions 19, 19' in each case meshing in an end toothing 16*a*, 16*a'* of the gear rack 16.

Figure 3:
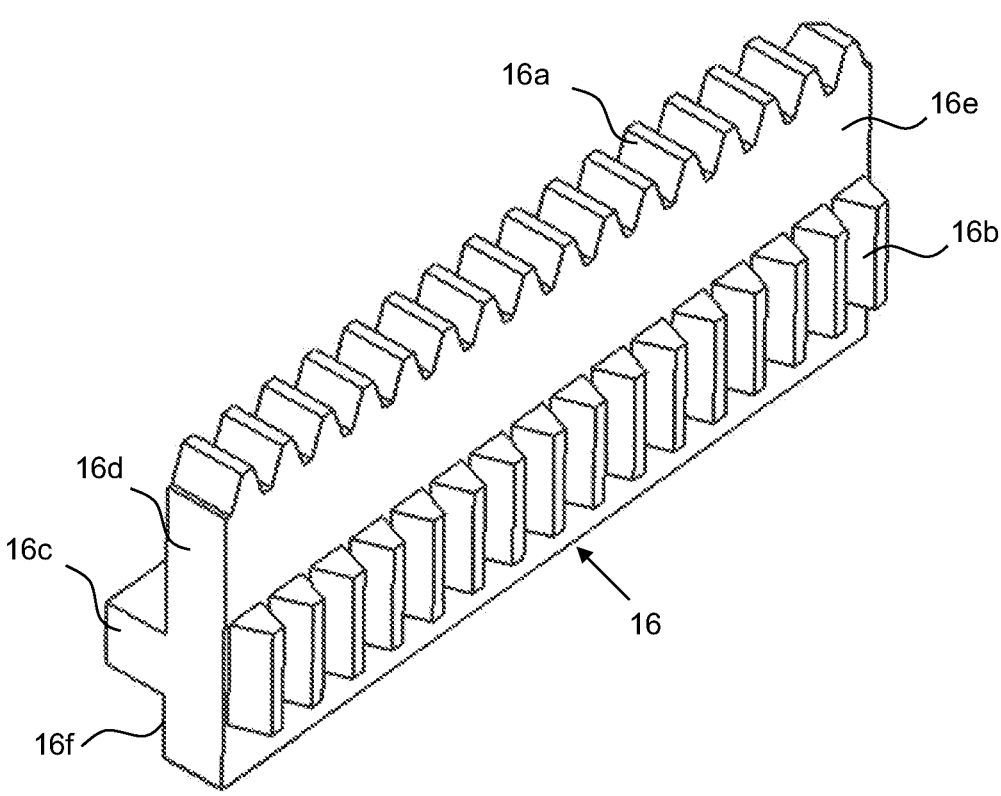
FIG. 3 shows a detailed view of the gear rack.

The gear rack 16 is depicted on its own in FIG. 3. The gear rack 16 is elongate and cuboid with narrow, short end faces 16*d* and long end faces or longitudinal end faces, one of which carries the end toothing 16*a*, and the side 16*f* facing away therefrom acts as a "projection", which can be accommodated in a guide groove 33*c*, see below, of the guide device.

A lateral toothing 16*b* is arranged along the length of the gear rack on the side face 16*e* (facing forward in FIG. 3). A rail (also to be considered a projection) 16*c* is formed on the second side face facing away from the lateral toothing 16*b* and likewise extends over the entire length of the gear rack 16.

In the steering gear 13, the gear rack 16 is movably mounted in a guide groove 33*c* which has been embedded in a bearing plate 34 (this also applies to the second gear rack 16'). The lower narrow side 16*f* of the gear rack 16 is partially accommodated in this guide groove 33*c*, and hence said gear rack is mounted therein.

The lateral rail 16*c* is located on or above the connection plate 34 and runs in the guide groove 33*a* of a guide block 33, which has been fastened to the top side of the bearing plate 34 by way of fastening means 33*b*, for example screws.

The gear racks 16, 16' are driven by motors 17, 17' by way of drive pinions 17*a*, 17*a'* which are fastened to drive shafts 17*b*, 17*b'* of the motors 17, 17' and whose respective axis of rotation corresponds to an axis of rotation C, C' of the motors 17, 17'. As a result of rotating the drive pinion 17*a*, 17*a'*, the gear rack 16, 16' is moved linearly in the grooves 33*c*, 33*a* in the direction of rotation, which is to say in the tangential direction of the transmission pinion 19, 19' perpendicular to the axis of rotation A and perpendicular to the drive axes C, C'. The tangential direction of rotation of the transmission pinion 19, 19' at the engagement with the gear rack 16, 16' is parallel to the instrument axis B in FIG. 2, corresponding to the movement direction of the gear rack 16.

Hence, the rotation of the motors 17, 17' and hence of drive pinions 17*a*, 17*a'*, corresponding to the axes of rotation C, C' of the motors 17, 17', is adopted by the lateral toothing 16*b*, 16*b'* of the gear rack 16, 16' and transferred to a linear movement of the gear rack 16, 16' parallel to the instrument axis B. In FIG. 2, these axes of rotation C, C' are parallel to an axis of rotation D of the third gear wheel 25 and fourth gear wheel 31. The linear movement of the gear rack 16, 16' is adopted by the transmission pinion 19, 19' and converted into a rotational movement of the respective double gear wheel 18, 18' around its axis of rotation A. The rotational movement of the double gear wheels 18, 18' then brings about a rotational movement of the third gear wheel 25 or fourth gear wheel 31 about its axis of rotation D, which is at right angles to the common axis A of the double gear wheels 18, 18', and hence brings about a movement of the wobble plate 14.

Figure 5:
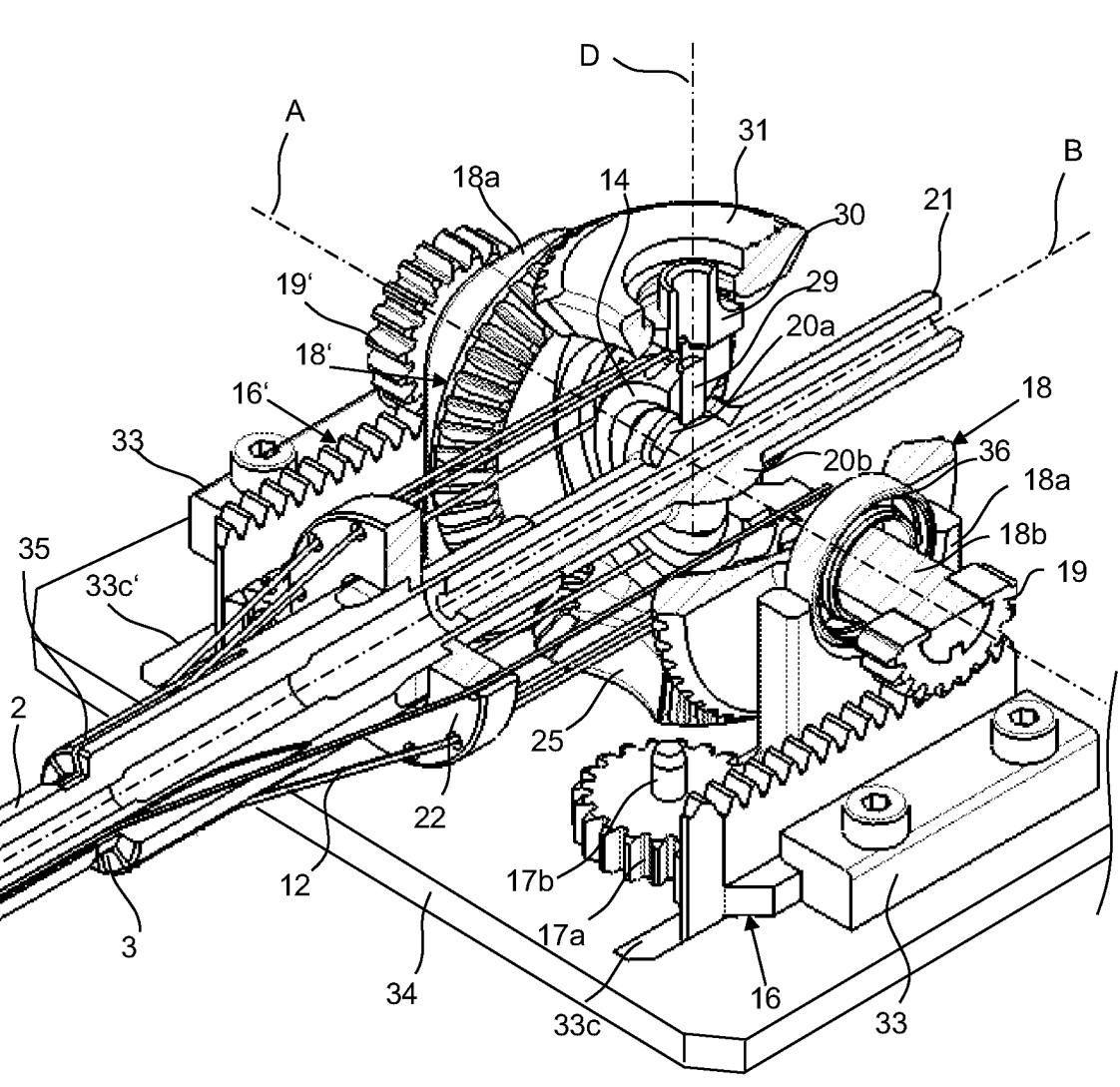
FIG. 5 shows a perspective, partly cut detailed view of the steering gear from FIG. 4.
Figure 6:
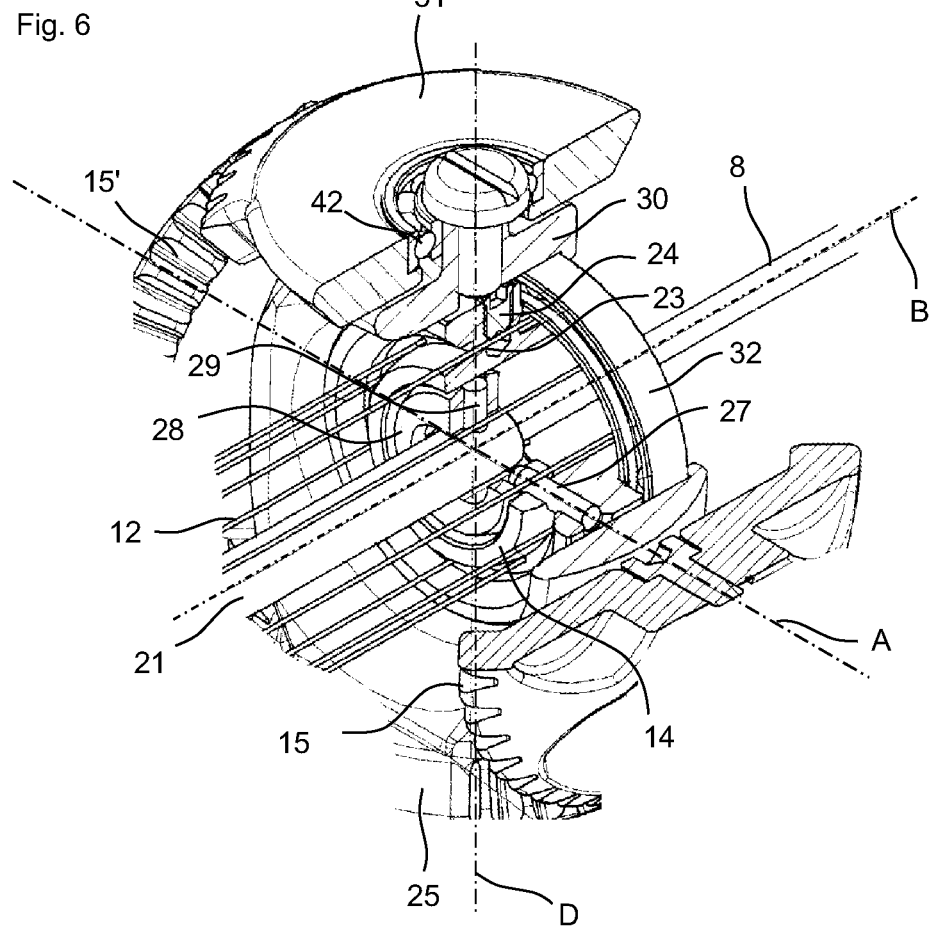
FIG. 6 shows a perspective, partly cut detailed view of the wobble plate gear according to a further embodiment.

The structure and operation of the steering gear 13 in relation to the control of the wobble plate 14 that is actuatable by the drive units and in relation to the mounting of said wobble plate are described below on the basis of FIGS. 4 to 6, wherein, for a better overview, only the bevel gears with the bevel gear rims 15, 15' of the double gear wheels 18, 18' are depicted in FIG. 6.

A hollow main shaft 21 which extends coaxially with respect to the longitudinal axis B of the shaft 2, which is rotatable about the longitudinal axis B of the shaft 2, and which extends beyond the proximal end 3 of the shaft 2 into the region of the steering gear 13 is arranged in the shaft 2 of the instrument 1. The actuation element 8 for actuating the instrument 7 is axially displaceably mounted within this hollow main shaft 21.

The steering wires 12 that emerge from the shaft 2 at the proximal end 3 of the shaft 2, for the purposes of which a shaft end piece 3 in which passage slots 33 for the steering wires 12 are provided can be provided at the proximal shaft end, are fanned open in the depicted examples by way of a fan plate 22 arranged for conjoint rotation with the main shaft 21 on the shaft end piece 3, thereby increasing the radial distance of the steering wires 12 from the longitudinal axis B of the shaft 2. While the diameter of the bundle of steering wires 12, which coaxially surround the longitudinal axis B of the shaft 2, is for example 4 mm within the shaft 2 or at the distal end 5 in the region of the angling mechanism 9, the said diameter of the bundle formed by the steering wires 12 is for example 18 mm behind the fan plate 22. The increase in the radial distance of the steering wires 12 from the longitudinal axis B of the shaft 2 obtained with the aid of the fan plate 22 not only simplifies the assembly and fabrication of the gear 13 equipped with the wobble plate 14 but also proportionally reduces the adjustment angle of the wobble plate 14 required for obtaining a desirably large pivot angle of the tool tip 6. With the increase in the diameter of the steering wire bundle from 4 mm within the shaft 2 to 18 mm behind the fan plate 22 described in exemplary fashion, the adjustment angle of the wobble plate 14 accordingly reduces 4.5-fold vis-à-vis the pivot angle of the tool tip 6 obtainable at the distal end. Thus, a pivot of the wobble plate 14 through only 20° is required to angle said tool tip through 90°.

On the proximal side behind the fan plate 22, the steering wires 12 running parallel to the longitudinal axis B of the shaft 2 are supplied to the wobble plate 14. In an alternative not depicted here, the steering wires 12 emerging at the proximal end 3 can run directly to the wobble plate 14 without the fan plate, with the result that the steering wires are supplied to the wobble plate 14 at an angle with respect to the longitudinal axis B. To secure the steering wires 12 on the wobble plate 14, drilled through holes 23 are formed in the wobble plate 14 for each steering wire 12, with the steering wires 12 in the example shown being frictionally connected and affixed to the wobble plate 14 within the drilled through holes 23 by way of setscrews 24. For example, alternative forms of fastening the steering wires to the wobble plate also comprise welding or crimping or other clamping devices.

The double gear wheels 18 and 18' as drive wheels are coupled to the third gear wheel 25 which by preference is in the form of a bevel gear and which meshes with the two bevel gear rims 15, 15' of the double gear wheels 18 and 18', with the result that the axis of rotation D of the third gear wheel 25 intersects the common axis of rotation A of the double gear wheels 18 and 18' and the longitudinal axis B of the shaft 2. As a result of the three meshing gear wheels 18, 18', and 25, every movement of the two double gear wheels 18 and 18' is directly transmitted to the wobble plate 14 that is coupled to the third gear wheel 25, bringing about a direct actuation of the steering wires 12.

To form a gimbal mount of the wobble plate 14 on the main shaft 21, the wobble plate 14 is pivotably mounted on a universal joint plate 28 by way of two bearing pins 27 arranged offset from one another by 180°, said universal joint plate in turn being pivotably mounted on the main shaft 21 by way of two bearing pins 29 arranged offset from one another by 180°. In FIG. 6, only one bearing pin 27 and one bearing pin 29 can be seen in each case on account of the partial sectional view.

In this case, the bearing pins 27 of the wobble plate 14 and the bearing pins 29 of the universal joint plate 28 are arranged offset from one another by 90°. This mount allows the wobble plate 14 to be pivoted relative to the longitudinal axis B of the shaft 2 about two axes at right angles to one another and allows a rotation of the main shaft 21 about the longitudinal axis B to be transmitted to the wobble plate 14, whereby, by way of the steering wires 12, the tool tip 6 (cf. FIG. 1) is pivotable in all spatial directions relative to the longitudinal axis B of the shaft 2 on the distal side.

Figure 4:
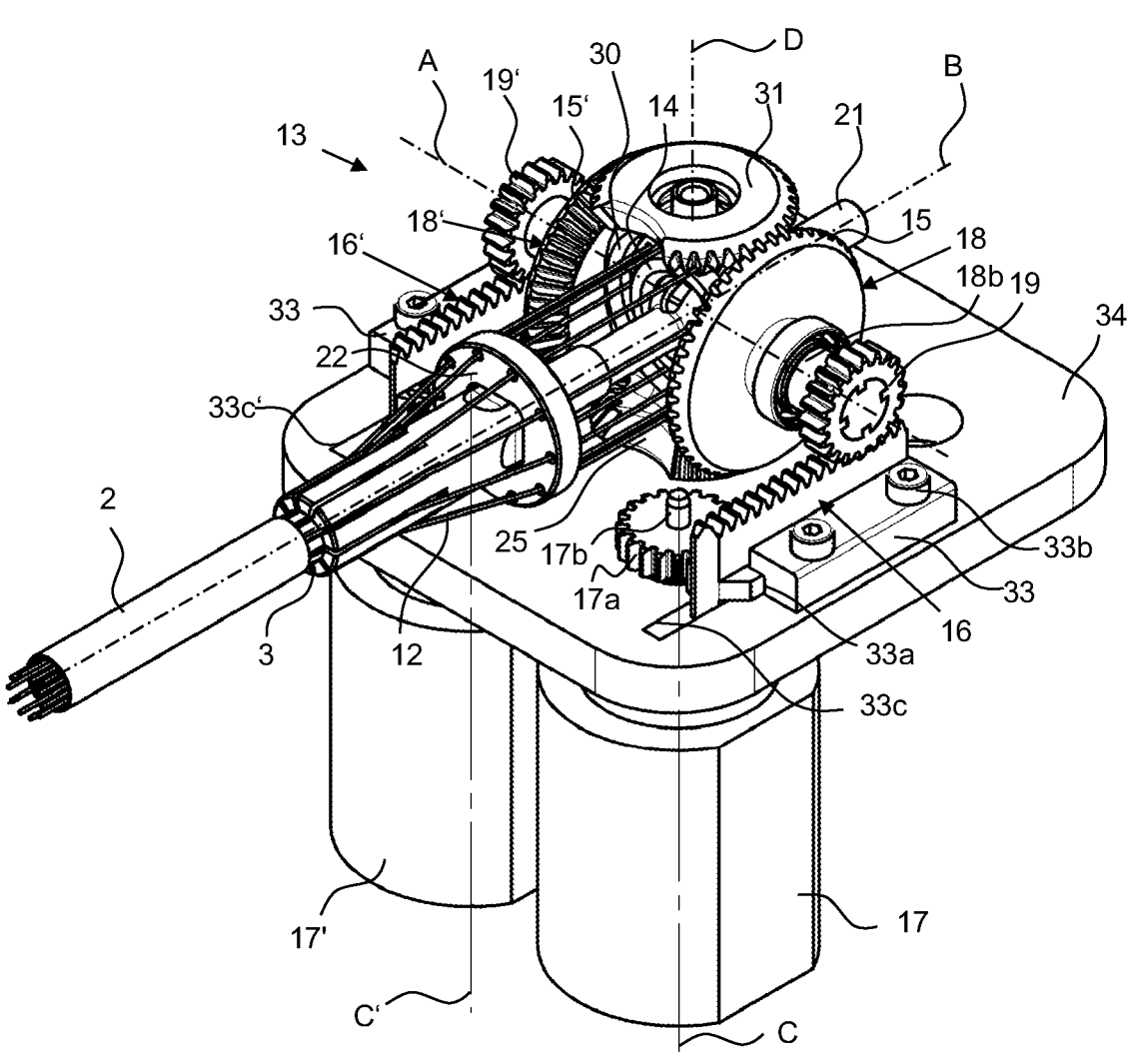
FIG. 4 shows a perspective view of a steering gear according to the invention as per a further embodiment.

The steering gear 13 depicted in FIGS. 4 and 5 has an alternative gimbal mount of the wobble plate 14 on the main shaft 21. This bearing arrangement, which is structurally simpler, more compactly designed, and easier to assemble, also allows pivoting of the wobble plate 14 about two degrees of freedom and rotation of said wobble plate about the longitudinal axis B, whereby, by way of the steering wires 12, the tool tip 6 is pivotable in all spatial directions relative to the longitudinal axis B of the shaft 2 on the distal side. In the region provided for mounting the wobble plate 14, the main shaft 21 in this case comprises two guide grooves 20a which extend along the main shaft 21 and are introduced into the main shaft 21 on both sides or diametrically, two pins 29 arranged diametrically on the wobble plate 14 in radially inwardly pointed fashion engaging in said guide grooves, with only one guide groove 20a with the pin 29 engaging therein being visible in FIG. 5. As a result of this engagement, the wobble plate 14 can be pivoted about both the axis of rotation D and the axis of rotation A from a neutral position, in which the wobble plate 14 is located in a plane which is defined by the axis of rotation A and perpendicular, which is to say at right angles, to the longitudinal axis B. Overlaid movements as a result of pivoting about both axes of rotation A, D are likewise possible. Further, the engagement of the pins 29 in the guide grooves 20a enables the transfer of a rotary angle of the main shaft 21 to the wobble plate 14, with the result that the wobble plate 14 can be displaced three-dimensionally relative to the longitudinal axis B of the shaft 2. The maximum tilt or twist or the maximum tilt and rotary angles about the axes of rotation A and D are determined by the length and depth of the guide grooves 20a in conjunction with the internal diameter and thickness of the wobble plate 14 and length of the pins 29. In the depicted example, the main shaft 21 comprises a spherical portion 20b in the region provided for mounting the wobble plate 14, the guide grooves 20a being present in said spherical portion and the latter securing the wobble plate 14 in the axial direction. In this case, the wobble plate 14 has a contoured accommodation recess matched to the spherical portion 20b.

As is also evident from FIGS. 2 and 4 to 6, the spatially adjustable wobble plate 14 is mounted in a steering ring 30 that is coupled for conjoint rotation with the third gear wheel 25. To close the toothing chain formed by the double gear wheels 18, 18' and gear wheel 25 to form a closed toothing ring which ensures a uniformly all-round force distribution, the fourth gear wheel 31, which is likewise by preference designed as a bevel gear and meshes with the bevel gear rims 15, 15' of the two double gear wheels 18 and 18', is arranged on the axis of rotation D of the third gear wheel 25 opposite to the third gear wheel 25.

By way of a bearing ring 32 (cf. FIG. 6), the wobble plate 14 is mounted in the steering ring 30 which is coupled for conjoint rotation with the third gear wheel 25, in order to allow a rotation of the wobble plate 14 about the longitudinal axis B of the shaft 2. The steering ring 30 coupled for conjoint rotation with the third gear wheel 25 is freely rotatable in relation to the fourth gear wheel 31 as a result of mounting by means of the bearing ring 42, with the result that a rotation of the fourth gear wheel 31 about its axis of rotation D does not bring about a twist of the steering ring 30 and wobble plate 14.

The described gimbal mount of the wobble plate 14 on the main shaft 21 allows the wobble plate 14 to be displaced three-dimensionally relative to the longitudinal axis B of the shaft 2. If, proceeding from the neutral initial position depicted in FIGS. 4 to 6, in which the wobble plate 14 is aligned perpendicular to the longitudinal axis B of the shaft 2, the double gear wheels 18 and 18' are driven by way of the motors 17, 17' such that the double gear wheels 18 and 18' rotate in the same direction, this twist of the double gear wheels 18 and 18', on account of the meshing engagement with the third gear wheel 25 and the fourth gear wheel 31, brings about a tilting of the assembly formed by the third gear wheel 25, the wobble plate 14 coupled to the third gear wheel 25 via the steering ring 30, and the fourth gear wheel 31, about the common axis of rotation A of the double gear wheels 18 and 18'. To simplify the functional description, the alignment of the bearing pins 27, 29 of the gimbal mount are referred to below in relation to the axes of rotation A and D. In fact, the bearing pins 27, 29 will no longer be flush with axes A and D as illustrated in the case of a rotation of the main shaft 21 and hence a rotation of the wobble plate 14, with the result that the pivot axes of the wobble plate 14 provided by the bearing pins 27, 29 may deviate from the axes of rotation A, D of the steering gear 13.

In the example of FIG. 6, this tilting of the wobble plate 14 relative to the main shaft 21 is enabled by the bearing pins 27, which are flush with the axis of rotation A of the double gear wheels 18 and 18' and by means of which the wobble plate 14 is pivotably mounted on the universal joint plate 28. This tilting of the wobble plate 14 about the axis of rotation A relative to the longitudinal axis B of the shaft 2 brings about, distally and by way of the steering wires 12, a corresponding pivot of the tool tip 6 relative to the longitudinal axis B of the shaft 2. In the example of FIGS. 4 and 5, the tilting of the wobble plate 14 about the axis of rotation A is enabled by the movement of the guide pins 29 in the guide grooves 20a in the spherical portion 20b of the main shaft 21.

If, proceeding from the neutral initial position depicted in FIGS. 4 to 6, in which the wobble plate 14 is aligned perpendicular to the longitudinal axis B of the shaft 2, the double gear wheels 18 and 18' are driven by way of the motors 17, 17' such that the double gear wheels 18 and 18' rotate in opposite directions, this twist of the double gear wheels 18 and 18', on account of the meshing engagement with the third gear wheel 25, brings about a twisting of the assembly formed by the third gear wheel 25 and the wobble plate 14 coupled to the third gear wheel 25 via the steering ring 30, about the axis of rotation D of the third gear wheel 25.

In the example of FIG. 6, this twisting of the universal joint plate 28 relative to the main shaft 21 is enabled by the bearing pins 29, which are flush with the axis of rotation D of the third gear wheel 25 and by means of which the universal joint plate 28 is pivotably mounted on the main shaft 21, together with the free rotatability of the wobble plate 14 relative to the fourth gear wheel 31 on account of the steering ring 32. This twisting of the wobble plate 14 about the axis of rotation D relative to the longitudinal axis B of the shaft 2 brings about, distally and by way of the steering wires 12, a corresponding pivot of the tool tip 6 relative to the longitudinal axis B of the shaft 2. In the example of FIGS. 4 and 5, the twisting of the wobble plate 14 about the axis of rotation D is brought about analogously by the pins 29 which engage in the guide grooves 20a and which are flush with the axis of rotation D of the third gear wheel 25.

Naturally, it is possible to overlay the movements described, with the result that, by way of example, the wobble plate 14 is tilted about the common axis of rotation A of the double gear wheels 18, 18' and, at the same time, is also additionally twisted about the axis of rotation D of the third gear wheel 25. As a result of combining the two sequences of motion on account of the individually controllable motors 17, 17' of the gear 13 and the coupling with the main shaft 21, it is possible to three-dimensionally adjust the wobble plate 14 relative to the longitudinal axis B of the shaft 2, from which a corresponding spatial displacement of the tool tip 6 results on account of the coupling via the steering wires 12.

A surgical instrument 1 embodied as described above is distinguished in that many thin steering wires 12 can be used to control the pivotable tool tip 6 and that, on account of the motorized drive 13 for the wobble plate 14 on which the steering wires 12 are mounted, this control can be sensitive, precise and reproducible.

An exemplary embodiment of the disclosure is depicted in the drawings. The drawings, the description, and the claims contain numerous features in combination. A person skilled in the art will advantageously also consider the features on an individual basis and combine them to form further advantageous combinations. The present disclosure provides a steering gear 13 for a surgical instrument 1, the steering gear 13 comprising two motorized drives and being designed to spatially align a wobble plate 14 by way of the adjustment angles of the two drives, the wobble plate being designed to control a distal angling mechanism 9 of the surgical instrument 1. In this case, a first of the two drives comprises a first motor 17 which drives a drive pinion 17a via a drive shaft 17b, said drive pinion meshing with a lateral toothing 16b of a first gear rack 16 and driving a first transmission pinion 19 of a first double gear wheel 18 made of the transmission pinion 19 and a bevel gear rim 15 via an end toothing 16a of the gear rack 16. A second of the two drives comprises a second motor 17' which drives a drive pinion 17*a*' via a drive shaft 17*b*', said drive pinion meshing with a lateral toothing 16*b*' of a second gear rack 16' and driving a second transmission pinion 19' of a second double gear wheel 18' made of the transmission pinion 19' and a bevel gear rim 15' via an end toothing 16*a*' of the gear rack 16'. In this case, the wobble plate 14 is arranged between the two bevel gear rims 15, 15' which face one another and are located on a common axis A. Further, a surgical instrument 1 having such a steering gear 13 is disclosed.

The invention claimed is:

1. A steering gear for a surgical instrument, the steering gear comprising:

two motorized drives configured to spatially align a wobble plate by way of the adjustment angles of the two motorized drives, the wobble plate being config- ured to control a distal angling mechanism of the surgical instrument, wherein a first of the two motorized drives includes a first motor which drives a first drive pinion via a first drive shaft, said first drive pinion meshing with a first lateral toothing of a first gear rack and driving a first trans- mission pinion of a first double gear wheel made of the first transmission pinion and a first bevel gear rim via a first end toothing of the first gear rack, and a second of the two motorized drives includes a second motor which drives a second drive pinion via a second drive shaft, said second drive pinion meshing with a second lateral toothing of a second gear rack and driving a second transmission pinion of a second double gear wheel made of the second transmission pinion and a second bevel gear rim via a second end toothing of the second gear rack, and wherein the wobble plate is arranged between the first bevel gear rim and the second bevel gear rim which face one another and are located on a common axis.

2. The steering gear as set forth in claim 1, wherein the respective orientations of a first and second drive axis of the corresponding first motor and the second motor are definable independently of one another and in relation to a plane defined by the longitudinal axis and the common axis, wherein a toothing of the corresponding first and second drive pinions with the respective first and second lateral toothings is formed depending on the orientation of the respective first and second drive axis, wherein the first drive axis of the first motor is preferably present parallel to the second drive axis of the second motor, wherein the first and second drive axes run perpendicular to the plane defined by the longitudinal axis and the common axis, and wherein the first and second drive pinions preferably form a spur toothing with the first and second lateral toothings.

3. The steering gear as set forth in claim 1, wherein the wobble plate is coupled to a third gear wheel which meshes with the first and the second bevel gear rims of the first and the second double gear wheels and whose axis of rotation is at right angles to the common axis of rotation of the driven first and second double gear wheels.

4. The steering gear as set forth in claim 1, wherein the wobble plate is coupled to a fourth gear wheel which is coupled to the two bevel gear rims (15, 15') of the two double gear wheels (18, 18') and arranged on the side of the wobble plate facing away from the third gear wheel.

5. The steering gear as set forth in claim 1, wherein each of the first gear rack-and the second gear rack are exten- sively and elongately cuboid, wherein the corresponding first end toothing and the second end toothing is present along a first longitudinal end face, and the corresponding first and second lateral toothings, which meshes with the respective first and second drive pinions, perpendicular to the end toothing along a side face.

6. The steering gear as set forth in claim 1, wherein the steering gear includes a bearing plate with a respective guide device for each of the first and the second gear racks, with each of the first and the second gear racks being mounted in its assigned guide device so as to be longitudinally mobile perpendicular to the common axis and, with the correspond- ing first and second end toothings, facing away from a top side of the bearing plate on which the first and second double gear wheels with the the first and second transmission pinions are arranged, wherein the first and the second motors are arranged on an underside of the bearing plate.

7. The steering gear as set forth in claim 6, wherein the guide devices each are a respective guide groove located in the bearing plate and running perpendicular to the common axis, wherein a lower guide portion on the side of the corresponding first and second gear racks facing away from the respective first and second end toothings is accommo- dated in the corresponding guide groove, and/or the guide devices are provided by at least one guide block arranged on the top side of the bearing plate and having a lateral guide groove which runs perpendicular to the common axis, points to the respective gear rack, and accommodates a longitudinal rail present on a side face of the gear rack facing away from the side face with the lateral toothing.

8. The steering gear as set forth in claim 6, wherein the respective side faces of the gear racks with the lateral toothing face the respective first and second double gear wheels.

9. The steering gear as set forth in claim 1, wherein each of the first and second double gear wheels comprises a bevel gear with the bevel gear rim which is connected to the transmission pinion with toothing all around via a gear shaft which extends along the common axis.

10. The steering gear as set forth in claim 9, characterized in that the gear shaft is rotatably mounted in a bearing eye component, wherein the bearing eye component is fastened to the bearing plate and aligned in relation to the axis of rotation of the respective first and second double gear wheels mounted in the bearing eye component with the gear shaft.

11. A surgical instrument comprising:

a shaft, an actuation unit arranged at the proximal end of the shaft, and an instrument arranged at the distal end of the shaft and having a tool tip which is able to be angled by means of a distal angling mechanism and controllable by a wobble plate that is spatially alignable by means of two drives, wherein the surgical instru- ment further includes the steering gear as set forth claim 1, the configured to transfer the adjustment angles of the two motorized drives to the spatial alignment of the wobble plate.

12. The surgical instrument as set forth in claim 11, further including a third gear wheel that meshes with the first and the second bevel gear rims of the first and the second double gear wheels, the wobble plate, via a bearing ring, is mounted so as to be rotatable about the longitudinal axis of the shaft in a steering ring that is coupled for conjoint rotation with the third gear wheel, the wobble plate being a gimbal-coupled to a main shaft running coaxially to a longitudinal axis of the shaft.

13. The surgical instrument as set forth in claim 11, wherein the wobble plate is pivotably mounted on a univer- sal joint plate by way of two bearing pins arranged offset from one another by 180°, wherein the universal joint plate is pivotally mounted on the main shaft by way of two bearing pins arranged offset from one another by 180°, and wherein the bearing pins (27, 29) of the wobble plate and universal joint plate are arranged offset from one another by 90°, or a gimbal mount is provided by two longitudinally extend-
      ing guide grooves diametrically present in the main
      shaft and two diametrically and radially inwardly point-
      ing pins arranged on the wobble plate, wherein each pin
      engages in one of the guide grooves such that a rotary
      angle of the main shaft is transferable to the wobble
      plate.

14. The surgical instrument as set forth in claim 11, wherein a fourth gear wheel is coupled to the wobble plate via a bearing ring with the steering ring, wherein the fourth gear wheel is freely rotatable vis-à-vis the third gear wheel.

15. The surgical instrument as set forth in claim 11 further including an actuation element that is axially displaceably mounted in the shaft and is operatively connected to the actuation unit on the proximal side, and in that the distal angling mechanism of the tool tip which is able to be angled consists of pivot members which are arranged at the distal end of the shaft and connected to the steering gear by way of steering wires running in the longitudinal direction of the shaft.

\* \* \* \* \*